US008652523B2

(12) United States Patent
Guimberteau et al.

(10) Patent No.: US 8,652,523 B2
(45) Date of Patent: *Feb. 18, 2014

(54) ORAL PHARMACEUTICAL FORMULATION IN THE FORM OF A PLURALITY OF MICROCAPSULES FOR PROLONGED RELEASE OF ACTIVE PRINCIPLE(S) WITH SLOW SOLUBILITY (75) Inventors: Florence Guimberteau, Montussan (FR); Catherine Castan, Orlienas (FR); Rémi Meyrueix, Lyons (FR)

(73) Assignee: Flamel Technologies, Venissieux (FR)

( * ) Notice: Subject to any disclaimer, the term of this patent is extended or adjusted under 35 U.S.C. 154(b) by 827 days.

This patent is subject to a terminal disclaimer.

(21) Appl. No.: 10/522,252

(22) PCT Filed: Jul. 28, 2003

(86) PCT No.: PCT/FR03/02382
§ 371 (c)(1),
(2), (4) Date: Feb. 15, 2006

(87) PCT Pub. No.: WO2004/010983
PCT Pub. Date: Feb. 5, 2004

(65) Prior Publication Data
US 2006/0165809 A1 Jul. 27, 2006

(30) Foreign Application Priority Data
Jul. 26, 2002 (FR) ...................................... 02 09532

(51) Int. Cl.
A61K 9/14 (2006.01)
A61K 9/16 (2006.01)

(52) U.S. Cl.
USPC ........... 424/489; 424/498; 424/490; 424/494; 424/497; 424/951; 424/963

(58) Field of Classification Search
None
See application file for complete search history.

(56) References Cited

U.S. PATENT DOCUMENTS

| 4,321,253 | A | 3/1982 | Beaty |
| 4,717,569 | A | 1/1988 | Harrison et al. |
| 4,748,023 | A | 5/1988 | Tamas et al. |
| 4,803,081 | A * | 2/1989 | Falk et al. ................ 424/488 |
| 4,894,240 | A | 1/1990 | Geoghegan et al. |
| 5,084,278 | A * | 1/1992 | Mehta ................ 424/441 |
| 5,286,497 | A | 2/1994 | Hendrickson et al. |
| 6,022,562 | A | 2/2000 | Autant et al. |
| 6,737,082 | B1 | 5/2004 | Picornell Darder |
| 6,946,146 | B2 * | 9/2005 | Mulye ................ 424/479 |
| 2006/0110463 | A1 | 5/2006 | Castan et al. |
| 2006/0165807 | A1 | 7/2006 | Castan et al. |

FOREIGN PATENT DOCUMENTS

| CA | 2068366 | | 11/1992 |
| EP | 0 207 041 | A2 | 12/1986 |
| EP | 0 207 041 | A3 | 12/1986 |
| EP | 0 249 587 | | 12/1987 |
| EP | 0 953 359 | | 11/1999 |
| FR | 2 313 915 | | 1/1977 |
| FR | 2 670 112 | A1 | 6/1992 |
| GB | 2 202 143 | | 9/1988 |
| JP | 61-001613 | | 1/1988 |
| JP | 08-073345 | | 3/1996 |
| JP | H09188617 | | 7/1997 |
| JP | 10-509427 | | 9/1998 |
| JP | 2000080028 | | 3/2000 |
| JP | 2000514059 | A | 10/2000 |
| JP | 2002521323 | A | 7/2002 |
| JP | 2003517470 | | 5/2003 |
| WO | WO 96/11675 | | 4/1996 |
| WO | WO-98/00116 | A1 | 1/1998 |
| WO | WO 99/49846 | | 10/1999 |
| WO | WO 00/18374 | | 4/2000 |
| WO | WO-01/37808 | A1 | 5/2001 |
| WO | WO 02/22108 | | 3/2002 |
| WO | WO 02/39984 | A2 | 5/2002 |

(Continued)

OTHER PUBLICATIONS

BASF, Volker Buhler, Generic Drug Formulations, Fine Chemicals (4th edition, 2001).*

(Continued)

Primary Examiner — Michael G Hartley
Assistant Examiner — Nabila Ebrahim
(74) Attorney, Agent, or Firm — Patton Boggs LLP (57) ABSTRACT The invention concerns microcapsules with prolonged release of active principles with low solubility, consisting of a core containing the active principle and coated with a polymer layer which controls the release of the active principle. The aim is that said oral microcapsules containing hardly soluble active principles, should have a coating film of sufficient thickness to ensure controlled permeability and should be adapted to industrial reproduction. This is achieved by the inventive microcapsules of mean diameter less than 1000 microns, and whereof the coating film contains a film-forming polymer (P1) insoluble in gastrointestinal tract fluids, a water-soluble polymer (P2), a plasticizer (PL), and optionally a lubricating surfactant (TA). Said microcapsules are characterized in that their coating films represents at least 3% p/p of dry matter, relative to their total weight and their core contains a hardly soluble active principle and a solubilizing agent (polyoxyethylene hydrogenated castor oil) which provides the core wherein it is contained with properties such that the behavior of the exposed core (non-coated) in a given dissolving test (TD), is as follows: release of 80% of active principle in less than two hours. The invention also concerns the use of such microcapsules in galenic formulation.

14 Claims, 2 Drawing Sheets

(56) References Cited

FOREIGN PATENT DOCUMENTS

| WO | WO 02/39984 A3 | 5/2002 |
| WO | WO 02/094285 A1 | 11/2002 |
| WO | WO-03/084517 | 10/2003 |
| WO | WO-03/084518 | 10/2003 |

OTHER PUBLICATIONS

Dubernet et al., "La Microencapsulation: Ses Techniques et ses Applications en Biologie," *L'actualite Chimique*, 1986, pp. 19-28.

* cited by examiner

ORAL PHARMACEUTICAL FORMULATION IN THE FORM OF A PLURALITY OF MICROCAPSULES FOR PROLONGED RELEASE OF ACTIVE PRINCIPLE(S) WITH SLOW SOLUBILITY

The field of the invention is that of the modified release of pharmaceutical active principles (APs) with low solubility.

In the present disclosure, the expression "modified release" denotes without distinction a release of the active principle(s) beginning as soon as the pharmaceutical form has been brought into contact with its dissolving medium (in vivo or in vitro) or else a release of the active principle(s) beginning only after a predetermined period of time ranging, for example, from 0.5 to several hours. Thus, for the purpose of the invention, a prolonging of the release corresponds to a release time for 50% of the active principle(s) which is typically several hours and which can extend from 0.25 to 20 hours, for example.

The expression "low solubility" relates to active principles the water-solubility of which is less than 10 g/l at 25° C.

More precisely, the invention relates to pharmaceutical formulations with prolonged release of active principles with low solubility, this formulation consisting of a plurality of microcapsules consisting of a core containing the active principle of low solubility and coated with a layer of polymer which controls the release of the AP.

Among the various modified-release systems, pharmaceutical systems with modified release consisting of a plurality of microcapsules of the reservoir type with an average diameter of less than 1000 microns are particularly advantageous. In fact, in these systems, the dose of active principle(s) to be administered is distributed among a large number of microcapsules (typically 10 000 for a dose of 500 mg and a diameter of 400 microns) and this type of system, as a result, has the following intrinsic advantages:

- the use of a mixture of microcapsules having different modified-release profiles makes it possible to produce release profiles exhibiting several waves of release or providing, by means of appropriate regulation of the various fractions, a constant plasma concentration level of the AP;
- the sensitivity to the variability of gastric emptying is lower, since the emptying, which takes place here with respect to a large number of particles, is statistically more reproducible;
- contact of the tissues with a high dose of AP, "dose dumping", is avoided. Each microcapsule in fact contains only a very low dose of active principle(s). The risk of tissue deterioration through local overconcentration of aggressive active principle(s) is thus avoided;
- it is possible to combine several pharmaceutical forms (immediate and/or delayed and/or prolonged release) comprising one or more active principles, in these "multimicro-capsular" systems;
- it does not induce any degradation of the AP;
- the amount of time spent by the microcapsules in the upper parts of the tract can be prolonged, which ensures an increase in the amount of time spent by the active principle(s) in passing in front of the absorption windows and thus maximizes the bioavailability of the active principle(s).

However, when the solubility of the AP is low, the production of a microparticulate modified-release form comes up against a substantial difficulty.

The diffusion of the active principle through the coating film surrounding each microcapsule takes place under the action of the dissolved AP concentration gradient between the inside and the outside of the microcapsule. In other words, it is the difference in osmotic pressure of the AP between the inside and the outside of the microcapsule which drives the release. The internal concentration of AP is the saturation concentration. The external concentration of AP is, for its part, negligible under usual conditions (termed "sink"). The driving of release is therefore directly linked to the saturation concentration of the AP, i.e. to its solubility.

For APs with low solubility, the saturation concentration of AP is relatively low and the diffusion of the AP to the outside is therefore, a priori, very slow, even for coating films that are not very thick.

Furthermore, in any case, for thin coating films, the following difficulties are encountered:

(a) The depositing of a very thin coating film is not even: there are gaps next to areas that are too thick, and the release of the AP is not prolonged.

(b) The industrial control of the process for a very thin deposit becomes very difficult and relatively unreproducible.

Moreover, for thicker coating films, the release of the AP is extremely slow, or even nonexistent.

The difficulty in modifying the release of an AP with low solubility explains the small number of technical solutions which have been proposed to date.

As regards the solid, multimicrocapsular pharmaceutical systems, those consisting of a multiplicity of particles or microcapsules each carrying active principle(s) coated with a film-coating layer based on ethylcellulose, on polyvinylpyrrolidone, on magnesium stearate and on castor oil, for example, are known. Such a pharmaceutical system is disclosed in PCT application WO 96/11675. These microcapsule reservoirs obtain an advantage from their multiplicity, which is a more even and reproducible gastric emptying time. In addition, their size is between 50 and 1000 μm and also the characteristics of their coating make it possible to increase their transit time in the upper parts of the gastrointestinal tract and, consequently, to maintain absorption of the active principle(s) for all or part of this time spent in the small intestine.

However, the multimicrocapsular pharmaceutical system according to WO 96/11675 is perfectable as regards APs with low solubility that can be administered orally, since it does not propose any solution to the problem of the diffusion of such an AP with low solubility through a coating film of sufficiently large thickness, for example of several microns.

As regards the prior art on microcapsules with modified release of active principles with low solubility, mention should first of all be made of PCT patent application WO 99/49846 which describes a pharmaceutical preparation composed of submicronic (0.05 to 10 μm) particles combining an active principle with low solubility with a phospholipid compound, a surface charge-modifying compound and a block polymer. The aim of this preparation is to improve the bioavailability and the stability of the active principle and it finds its applications in injectable forms or alternatively in forms intended to be administered ocularly or nasally. A prolonged-release form is only obtained in the case of intramuscular injection.

PCT patent application WO 00/18374 describes an invention of the same type as the previous one: the active principle in the form of submicronic (<1000 nm) particles is stabilized by a compound associated at the surface of the particles and mixed with a polymer. This mixture can then be formulated into granules or pellets and, optionally, into tablets. The active principle is rapidly dissolved and it is the increase in bioavailability obtained by virtue of the decrease in size which makes it possible to have an effective plasma concentration over a prolonged period.

Patent application GB-2 202 143 describes spheroids of diameter greater than 0.5 mm, and preferably greater than 0.8 mm, containing the poorly soluble active principle dispersed in 70 to 99.5% of microcrystalline cellulose. This matricial form requires no coating controlling the release of the active principle.

Patent application JP-8073345 describes a controlled-release system composed of a film-coated granule. The granule contains an active principle with low solubility at neutral pH and inorganic acids. This system therefore proposes a solution that is only suitable for the case of basic active principles with low solubility.

Finally, European patent EP-B-0 249 587 concerns a solid preparation for the slow release of an active substance with low solubility (<0.1% by weight). This controlled-release preparation can be provided in the form of gelatin capsules comprising capsules consisting of coated granules. The granules comprise the active principle with low solubility and a solubilizing agent consisting of the commercial product Cremophor® RH 40 (polyoxyethylenated hydrogenated castor oil: 40 ethylene oxide units), and also other additives such as polyvinylpyrrolidone, cellulose, starch and lactose. These granules of size of between 700 and 1120 μm are covered with an ethylcellulose coating layer for controlling release. The ingredients of the granules, namely polyvinylpyrrolidone, cellulose, cornstarch and lactose, appear to be the elements of the hydrophilic gel system specific to the pharmaceutical form according to EP-B-0 249 587. These capsules therefore comprise a single constituent (ethylcellulose) in their coating layer, which limits its capacities in terms of modification of the release of the active principle. In particular, it is doubtful whether a coating layer composed only of ethylcellulose (known to form impermeable films) would allow the release of an AP with low solubility in a controlled and industrially reproducible manner over a period of several hours, for example.

None of these patent applications describes microparticles of the reservoir type or microcapsules for which the prolonged release of the active principle with low solubility is controlled by means of its diffusion through a membrane that is sufficiently thick to ensure a controlled and industrially reproducible permeability. Neither do they teach the manner in which such a system can be successfully achieved.

In the face of this vacuity of the prior art, one of the essential objectives of the present invention is to propose a form with modified release of AP(s) with low solubility consisting of a plurality of microcapsules, each formed by a core containing the AP and coated with a coating film.

Another objective of the present invention is to provide a plurality of reservoir-type microcapsules of AP of low solubility, for oral administration of the latter, the coating film of these microcapsules being sufficiently thick to ensure a controlled and industrially reproducible permeability.

Another essential objective of the present invention is to provide a plurality of microcapsules of AP(s) with low solubility, less than 1000 μm in size.

Another objective of the present invention is to propose an oral pharmaceutical form consisting of a large number (for example of the order of several thousand) of microcapsules, this multiplicity ensuring, statistically, good reproducibility of the kinetics of transit of the AP in the entire gastrointestinal tract, such that better control of the bioavailability and therefore better effectiveness result therefrom.

Another essential objective of the present invention is to provide a plurality of microcapsules of AP(s) with low solubility, for oral administration of the latter according to a prolonged and/or optionally delayed release profile, such that the half-release time, $t_{1/2}$, is between 0.25 and 20 hours.

Another essential objective of the present invention is to provide an oral form with modified release in which the AP(s) is (are) in the form of a plurality of particles individually coated to form microcapsules, and in which it is possible to mix several active principles in multimicrocapsular form, that are released according to different respective release times.

Having set themselves all the above objectives among others, the inventors have, to their credit, developed a multimicrocapsular pharmaceutical system with prolonged release of AP(s) with low solubility:

which makes it possible to adjust the AP half-release time to between 0.25 and 20 hours, which is reproducible and easy to implement industrially by virtue of a ratio of the mass of the coating film to the mass of the particle of greater than 3% dry weight/dry weight, preferably greater than 5% dry weight/dry weight, and even more preferably of between 3 and 40% dry weight/dry weight.

To do this, the inventors have, to their credit, discovered after many trials, microcapsules with a particular structure which make it possible to satisfy the objectives recalled above, among others.

Thus, the invention relates to microcapsules for the modified release of at least one AP with low solubility, intended to be administered orally and of the type of those:

each consisting of a core comprising at least one active principle and of a coating film applied onto the core and controlling the prolonged release of the AP(s), the mean diameter of which is less than 1000 microns, preferably between 800 and 50 microns, and even more preferably between 600 and 100 microns, in which the coating film of each microcapsule contains the following components:

→-I—at least one film-forming polymer (P1) insoluble in gastrointestinal tract fluids, →-II—at least one water-soluble polymer (P2), →-III—at least one plasticizer (PL), →-IV—and, optionally, at least one lubricating surfactant (TA);

characterized in that:

➤ their coating film represents at least 3% dry weight/dry weight, preferably at least 5% dry weight/dry weight of their total mass, ➤ their core contains at least one AP and at least one solubilizing agent having the particularity, as soon as it is placed in aqueous solution at a concentration of 20% w/w at 37° C., of increasing the solubility of the AP by more than 50%.

It is interesting to note that this original structure of microcapsules with a core comprising a solubilizing agent and a coating based on P1/P2/PL/(TA) is designed in such a way as to significantly improve the solubility of the AP in aqueous solution. In order to achieve this, the microcapsules according to the invention are in fact prepared in such a way that they facilitate the dampening of the surface of the AP crystals with water.

The solubility of the active principle is, for example, measured by introducing the AP into an aqueous solution containing the solubilizing agent. The solution is stirred at 37° C. for 6 hours and then filtered through a filter with a 0.2 μm pore diameter. The content of solubilized AP is evaluated by HPLC chromatography or any other suitable analytical technique.

Preferably, the components P1, P2 and PL of the coating film satisfy the following characteristics:
- mass fraction by dry weight of P1 relative to the total mass of the coating of between 40 and 90%, and preferably of between 50 and 80%;
- mass fraction by dry weight P2/P1+P2 of between 15 and 60%, and preferably of between 15 and 55%;
- mass fraction by dry weight PL/P1+PL of between 1 and 30%, and preferably of between 5 and 25%.

According to an advantageous variant, the coating film comprises component TA in a proportion of 2 and 20%, and preferably of between 4 and 15% of the total mass of the dry coating.

Preferably, the coating film represents 3 to 40% dry weight/dry weight of the total mass of the microcapsules.

In accordance with preferred embodiments of the invention, the core containing the AP and the solubilizing agent may have either of the following structures:

Structure A
The core consists of a microbead approved for chronic oral administration, composed, for example and without implied limitation, of cellulose derivatives and/or of hydrophilic compounds such as sucrose and/or dextrose, etc. This neutral core is covered with a layer comprising a mixture of the AP and of at least one solubilizing agent as defined hereinafter.

Structure B
The core is composed of a monocrystal of AP coated with a layer containing the solubilizing agent defined hereinafter.

Structure C
The core is a granule composed of the mixture of the AP(s), of one or more granulation excipients known to those skilled in the art and of one or more solubilizing agents defined hereinafter.

Besides the fact that they make it possible to solve the technical problem that is the basis of the invention, one of the many advantageous characteristics of these solubilizing agents is that they belong to the family of pharmaceutical excipients approved, for chronic oral administration, by most of the relevant authorities in this respect throughout the world.

In addition, these solubilizing agents are selected such that they do not induce any degradation of the AP.

Advantageously, the solubilizing agent(s) present in the core with the AP confer(s), on the core in which it (they) is (are) included, properties such that the behavior of the exposed (non-coated) core in a given dissolving test TD defined in the examples below is as follows: release of 80% of the AP in less than two hours, preferably in less than one hour.

These solubilizing agents are preferably chosen, in a non-exhaustive manner, from the following families:

(a) hydrophilic polymers, preferably:
- polyvinyl pyrrolidone,
- polyvinyl alcohol,
- hydrophilic derivatives of cellulose, preferably hydroxypropylcellulose and/or carboxymethylcellulose,
- maltodextrins,
- polyethylene glycol (PEG);

(b) surfactants, preferably:
- polyoxyethylene-polyoxypropylene copolymers,
- polyoxyethylenated hydrogenated castor oil,
- sodium dodecyl sulfate,
- esters of sucrose and of sorbitan,
- phospholipids,
- polyethylene glycol (PEG) stearate,
- disodium pamoate,
- polyoxyethylenated oils,
- polysorbates;

(c) or else from sequestering agents, preferably cyclodextrins;

(d) and mixtures thereof.

According to a preferred characteristic of the invention, the mass fraction [solubilizing agent]×100/[solubilizing agent+AP] is greater than or equal to 5%, and preferably between 10 and 98%.

Preferably, P1 is selected from the group of products below:
- water-insoluble derivatives of cellulose, preferably ethylcellulose and/or cellulose acetate,
- acrylic derivatives,
- poly(vinyl acetates),
- and mixtures thereof.

Preferably, P2 is selected from the group of products below:
- water-soluble derivatives of cellulose,
- polyacrylamides,
- poly-N-vinylamides,
- poly(N-vinyl lactams),
- polyvinyl alcohols (PVAs),
- polyoxyethylenes (POEs),
- polyvinylpyrrolidones (PVPs) (the latter being preferred),
- and mixtures thereof.

Preferably, PL is selected from the group of products below:
- glycerol and esters thereof, preferably from the following subgroup:
  - acetylated glycerides, glyceryl monostearate, glyceryl triacetate, glyceryl tributyrate,
- phthalates, preferably from the following subgroup:
  - dibutyl phthalate, diethyl phthalate, dimethyl phthalate, dioctyl phthalate,
- citrates, preferably from the following subgroup:
  - acetyl tributyl citrate, acetyl triethyl citrate, tributyl citrate, triethyl citrate,
- sebacates, preferably from the following subgroup:
  - diethyl sebacate, dibutyl sebacate,
- adipates,
- azelates,
- benzoates,
- plant oils,
- fumarates, preferably diethyl fumarate,
- malates, preferably diethyl malate,
- oxalates, preferably diethyl oxalate,
- succinates, preferably dibutyl succinate,
- butyrates,
- cetyl alcohol esters,
- salicylic acid,
- triacetin,
- malonates, preferably diethyl malonate,
- cutin,
- castor oil (this being particularly preferred),
- and mixtures thereof.

Preferably, TA is selected from the group of products below:
- anionic surfactants, preferably from the subgroup of alkali metal salts or alkaline-earth metal salts of fatty acids, stearic acid and/or oleic acid being preferred,
- and/or nonionic surfactants, preferably from the following subgroup:
  - polyoxyethylenated oils, preferably polyoxyethylenated hydrogenated castor oil,
  - polyoxyethylene-polyoxypropylene copolymers,
  - polyoxyethylenated sorbitan esters, polyoxyethylenated castor oil derivatives,
stearates, preferably calcium stearate, magnesium stearate, aluminum stearate or zinc stearate,
stearyl fumarates, preferably sodium stearyl fumarate, glyceryl behenate,
and mixtures thereof.

This preparation according to the invention makes it possible to produce a multimicrocapsular form with modified release of APs with low solubility, it being possible for the AP half-release time to be adjusted to between 0.25 and 20 hours in a reproducible manner through the use of a coating film, that can be described as a diffusion coating film, which is sufficiently thick.

Moreover, for APs with low solubility for which the absorption window is limited, such a plurality of microcapsules (typically 10 000 for a dose of 500 mg and a mean diameter of 400 microns) has the following intrinsic advantages:

The use of a mixture of microcapsules having different delayed- and controlled-release profiles makes it possible to produce release profiles exhibiting several waves of release or providing, by means of adequate regulation of the various fractions, a constant plasma concentration level of the AP.

The variability of gastric emptying is lower, since the emptying, which takes place here with respect to a large number of particles, is statistically more reproducible.

Contact of the tissues with a high dose of AP, "dose dumping", is avoided. Each microcapsule in fact contains only a very low dose of AP. The risk of tissue deterioration through a local overconcentration of aggressive AP is thus avoided.

The amount of time spent by the microcapsules in the upper parts of the tract can be prolonged, which ensures an increase in the amount of time spent by the AP in passing in front of the absorption windows and thus maximizes the bioavailability of the AP.

The APs with low solubility used for preparing the modified-release, preferably controlled-release, microcapsules according to the invention can be chosen from at least one of the major varieties of active substances below:
antiulcer agents, antidiabetic agents, anticoagulants, antithrombics, blood lipid-lowering agents, anti-arrhythmics, vasodilators, antiangina agents, anti-hypertensives, vasoprotective agents, fertility promoters, inducers and inhibitors of uterine labor, contraceptives, antibiotics, antifungal agents, anti-viral agents, anticancer agents, anti-inflammatories, analgesics, antiepileptics, antiparkinsonian agents, neuroleptics, hypnotics, anxiolytics, psychostimulants, antimigraine agents, antidepressives, antitussives, antihistamines or anti-allergic agents.

Preferably, the AP(s) is (are) chosen from the following compounds: prazosine, acyclovir, nifedipine, naproxen, ibuprofen, ketoprofen, fenoprofen, indomethacine, diclofenac, sulpiride, terfenadine, carbamazepine, fluoxetine, alprazolam, famotidine, ganciclovir, spironolactone, acetylsalicyclic acid, quinidine, morphine, amoxicillin, paracetamol, metoclopramide, verapamil and mixtures thereof.

As regards the preparation of the microcapsules according to the invention, this goes back to micro-encapsulation techniques accessible to those skilled in the art, the principles of which are summarized in the article by C. Duverney and J. P. Benoit in "L'actualitéchimique" [Current use in chemistry], December 1986. More precisely, the technique under consideration is microencapsulation by film-coating, resulting in individualized "reservoir" systems as opposed to matricial systems.

For further details, reference will be made to patent EP-B-0 953 359.

The AP particles of desired mean particle size necessary for preparing the microcapsules according to the invention may be crystals of pure AP and/or AP that has undergone a pretreatment by one of the conventional techniques in the field, such as for example granulation, in the presence of at least one conventional binding agent and/or of an agent for modifying the intrinsic solubility characteristics of the AP.

The present invention is also directed toward a medicinal product comprising the microcapsules as defined above.

This medicinal product may be in solid form: tablet, gelatin capsule, powder, etc, or a in liquid form, for example an aqueous suspension.

In accordance with the invention, it is also proposed, as a solution to the problems mentioned at the beginning of the present disclosure, namely: modified, preferably prolonged, release of APs with low solubility, in a pharmaceutical form that can be readily swallowed, all this in a perspective of long, effective and safe therapeutic coverage, to use a plurality of microcapsules:
each consisting of a core comprising at least one active principle and of a coating film applied onto the core and controlling the prolonged release of the AP(s),
the mean diameter of which is less than 1000 microns, preferably between 800 and 50 microns, and even more preferably between 600 and 100 microns,
in which the coating film of each microcapsule contains the following components:
→-I—at least one film-forming polymer (P1) insoluble in gastrointestinal tract fluids,
→-II—at least one water-soluble polymer (P2),
→-III—at least one plasticizer (PL),
→-IV—and, optionally, at least one lubricating surfactant (TA);
characterized in that:
➢ the coating film of the microcapsules represents at least 3% dry weight/dry weight, preferably at least 5% dry weight/dry weight of the total mass,
➢ and their core contains at least one AP and at least one solubilizing agent having the particularity, as soon as it is placed in aqueous solution at a concentration of 20% w/w at 37° C., of increasing the solubility of the AP by more than 50%,
for producing a medicinal product based on at least one AP with low solubility which can be administered orally, which can be readily swallowed, and which is released in vivo in a controlled, prolonged and, optionally, delayed manner.

According to yet another of its objects, the present invention relates to a method of therapeutic treatment, in which use is made of a medicinal product as defined above as a product per se or as a product obtained by means of the method described above.

The invention will be understood more fully, in terms of its composition and the properties and obtaining thereof, on reading the examples below, given only by way of illustration and making it possible to highlight the variants of implementation and the advantages of the invention.

EXAMPLE 1

1.1—Preparation of Spironolactone Microcapsules:

Step 1: Granule 180 g of spironolactone, 100 g of polyoxyethylenated hydrogenated castor oil (40 ethylene oxide units), sold under the trademark Cremophor® RH 40, and 120 g of povidone (Plasdone® K29/32) are solubilized beforehand in a water/acetone/isopropanol (5/57/38 m/m) mixture. This solution is then sprayed onto 800 g of Celphere® CP-305 cellulose spheres (Asahi Kasei; diameter of between 300 and 500 µm) in a Glatt® GPC-G1 fluidized air bed device.

Step 2: Coating 50 g of granules obtained above are coated with 1.60 g of ethylcellulose (Ethocel® 7 Premium), 0.16 g of dibutyl sebacate, 0.64 g of polyoxyethylenated hydrogenated castor oil (40 ethylene oxide units), sold under the trademark Cremophor® RH 40 and 0.80 g of povidone (Plasdone® K29/32) dissolved in an acetone/isopropanol (60/40 m/m) mixture, in a miniGlatt fluidized air bed device.

1.2—Microcapsule Composition:

TABLE 1

| Ingredients | % by mass | Production formula (in g) |
| --- | --- | --- |
| Spironolactone granules | 94.00 | 50 |
| cellulose spheres | (62.7) | |
| Plasdone ® K29/32 | (9.4) | |
| Cremophor ® RH 40 | (7.8) | |
| Spironolactone | (14.1) | |
| Coating | 6.00 | 3.2 |
| Ethocel ® 7 Premium | (3.0) | |
| Plasdone ® K29/32 | (1.5) | |
| Cremophor ® RH 40 | (1.2) | |
| Dibutyl sebacate | (0.3) | |

1.3—Increase in Solubility

In an aqueous solution at pH 6.8 and comprising 20% by weight of Cremophor® RH 40, the solubility at 25° C. of the spironolactone, which, without solubilizing agent, is of the order of 38 mg/l, is multiplied by a factor of 5.

1.4—Dissolving Test (TD):

The kinetics of release of the spironolactone are determined by means of a dissolving test (type II device according to the European pharmacopoeia, 3rd edition, phosphate buffer medium, pH 6.8; volume 1000 ml, temperature 37° C., 100 rpm paddle agitation, UV detection at 240 nm).

The TD test is first of all carried out on noncoated granules, and then on microcapsules comprising these granules.

TD Test Result:

Noncoated granules: release is complete (greater than 97% dissolution) at t=1 hour.

Figure 1:
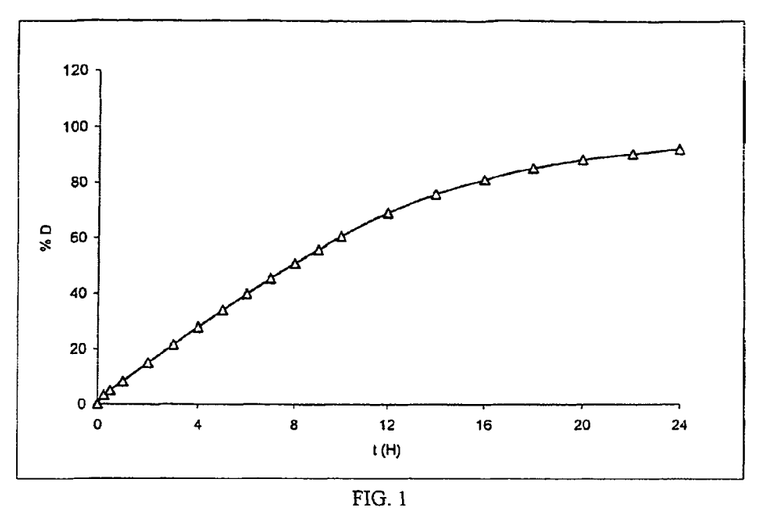
FIG. 1 represents the curve of the percentage of dissolved AP (% D) as a function of the time (t) in hours (H), of the microcapsules of example 1, in the dissolving test TD.

Microcapsules: the result is given in the attached FIG. 1.

The microcapsule composition described above makes it possible to obtain a modified-release profile over 8 h for very low-solubility spironolactone (0.02 g/l). The membrane represents 6% of the weight of the microcapsule, which ensures a release profile that is reproducible in an industrial process.

EXAMPLE 2

2.1—Preparation of Spironolactone Microcapsules:

Step 1: Granule 180 g of spironolactone, 100 g of polyoxyethylenated hydrogenated castor oil (40 ethylene oxide units), sold under the trademark Cremophor® RH 40, and 120 g of povidone (Plasdone® K29/32) are solubilized beforehand in a water/acetone/isopropanol (5/57/38 m/m) mixture. This solution is then sprayed onto 800 g of cellulose spheres (diameter of between 300 and 500 µm) in a Glatt® GPC-G1 fluidized air bed device.

Step 2: Coating 50 g of granules obtained above are coated with 1.44 g of ethylcellulose (Ethocel® 7 Premium), 0.16 g of castor oil, 0.64 g of polyoxyethylene-polyoxypropylene copolymers (Lutrol® F-68) and 0.96 g of povidone (Plasdone® K29/32) dissolved in an acetone/isopropanol (60/40 m/m) mixture, in a miniGlatt® fluidized air bed device.

2.2—Microcapsule Composition:

TABLE 2

| Ingredients | % by mass | Production formula (in g) |
| --- | --- | --- |
| Spirono lactone granules | 94.00 | 50 |
| cellulose spheres | (62.7) | |
| Plasdone ® K29/32 | (9.4) | |
| Cremophor ® RH 40 | (7.8) | |
| Spironolactone | (14.1) | |
| Coating | 6.00 | 3.2 |
| Ethocel ® 7 Premium | (2.7) | |
| Plasdone ® K29/32 | (1.8) | |
| Lutrol F-68 | (1.2) | |
| Castor oil | (0.3) | |

2.3—TD Test:

The kinetics of release of the spironolactone are determined by means of a dissolving test (type II device according to the European pharmacopoeia, 3rd edition, phosphate buffer medium, pH 6.8, volume 1000 ml, temperature 37° C., 100 rpm paddle agitation, UV detection at 240 nm).

Figure 2:
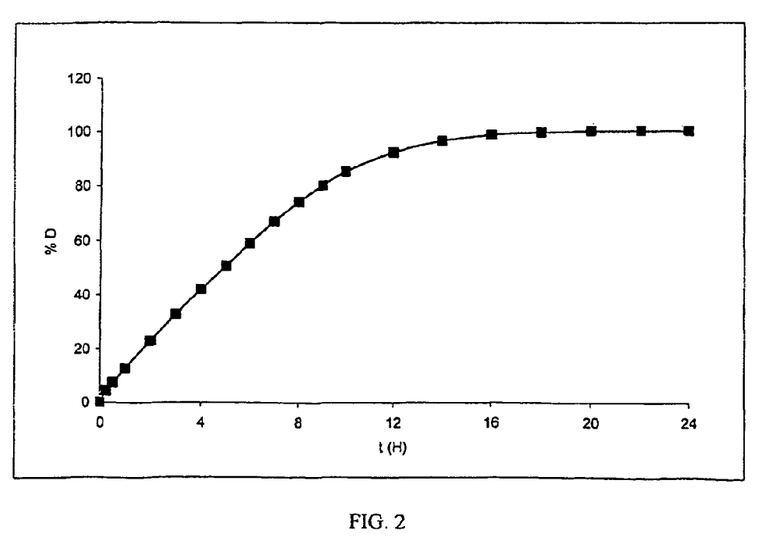
FIG. 2 represents the curve of the percentage of dissolved AP (% D) as a function of the time (t) in hours (H), of the microcapsules of example 2, in the dissolving test TD.

TD test result:

The result is given in attached FIG. 2.

The microcapsule composition described above makes it possible to obtain a modified-release profile over 8 h for very-low solubility spironolactone (0.02 g/l). The membrane represents 6% of the weight of the microcapsule, which ensures a release profile that is reproducible in an industrial process.

EXAMPLE 3

3.1—Preparation of Spironolactone Microcapsules:

Step 1: Granule 35 g of spironolactone, 2.5 g of polyoxyethylenated hydrogenated castor oil (40 ethylene oxide units), sold under the trademark Cremophor® RH 40, 12.5 g of povidone (Plasdone® K29/32) and 200 g of lactose are dry-mixed beforehand in a laboratory granulator (Mi-PRO/Pro-C-ept) for 5 minutes. This pulverulent mixture is then granulated with water (20 g). The granules are dried at 40° C. in a ventilated oven, and then sized on a 500 µm screen. The 200-500 µm fraction is selected by sieving.

Step 2: Coating 50 g of granules obtained above are coated with 1.88 g of ethylcellulose (Ethocel® 7 Premium), 0.23 g of castor oil, 0.75 g of polyoxyethylenated hydrogenated castor oil (40 ethylene oxide units), sold under the trademark Cremophor® RH 40, and 0.90 g of povidone (Plasdone® K29/32) dissolved in an acetone/isopropanol (60/40 m/m) mixture, in a miniGlatt fluidized air bed device.

3.2—Microcapsule Composition:

TABLE 3

| Ingredients | % by mass | Production formula (in g) |
| --- | --- | --- |
| Spironolactone granules | 93.00 | 50 |
| Lactose | (74.40) | |
| Plasdone ® K29/32 | (4.65) | |
| Cremophor ® RH 40 | (0.93) | |
| Spironolactone | (13.02) | |
| Coating | 7.00 | 3.76 |
| Ethocel ® 7 Premium | (3.50) | |
| Plasdone ® K29/32 | (1.68) | |
| Cremophor ® RH 40 | (1.40) | |
| Castor oil | (0.42) | |

3.3—Test:

The kinetics of release of the spironolactone are determined by means of a dissolving test (type II device according to the European pharmacopoeia, 3rd edition, phosphate buffer medium, pH 6.8, volume 1000 ml, temperature 37° C., 100 rpm paddle agitation, UV detection at 240 nm).

Figure 3:
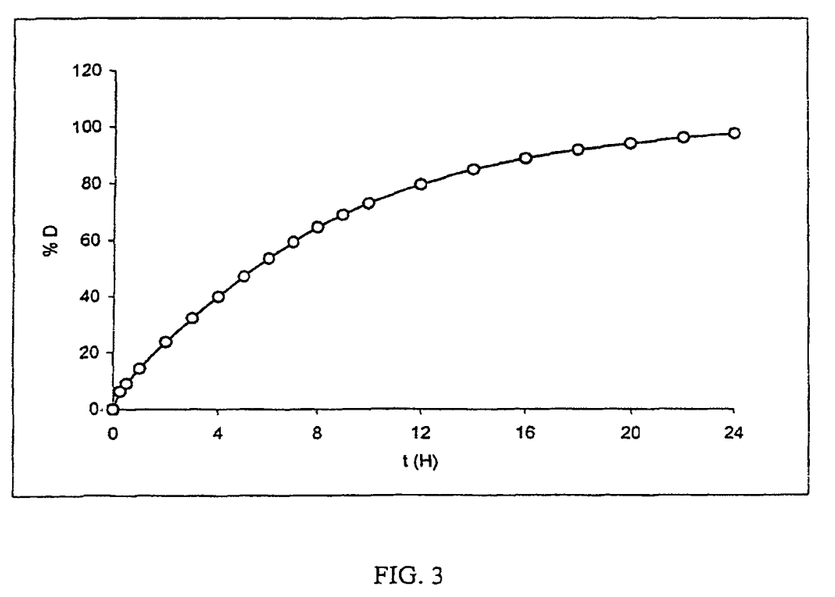
FIG. 3 represents the curve of the percentage of dissolved AP (% D) as a function of the time (t) in hours (H), of the microcapsules of example 3, in the dissolving test TD.

TD test result:

The result is given in attached FIG. 3.

The microcapsule composition described above makes it possible to obtain a modified-release profile over 12 h for very-low solubility spironolactone (0.02 g/l). The membrane represents 7% of the weight of the microcapsule, which ensures a release profile that is reproducible in an industrial process.

EXAMPLE 4

The ability of the solubilizing agent, made of Cremophor® RH 40, to solubilize an active principle, made up of spironolactone, is tested according to the following method for measuring solubility:

The AP is introduced into an aqueous solution containing the solubilizing agent. The solution is stirred at 37° C. for 6 hours and is then filtered through a filter with a 0.2 μm pore diameter. The content of solubilized AP is evaluated by HPLC. The results are given in table 4 below:

TABLE 4

| Cremophor ® RH 40 % w/w at 37° C. | (Spironolactone) dissolved in solution mg/ml |
| --- | --- |
| 0 | <0.1 |
| 1 | 0.1 |
| 2 | 0.2 |
| 5 | 0.4 |
| 10 | 0.8 |
| 20 | 1.4 |

The invention claimed is:

1. Orally administered microcapsules for modified release of at least one active principle with low solubility,
wherein the mean diameter of the microcapsules are less than 1000 microns;
wherein each microcapsule has a core comprising at least one active principle and at least one solubilizing agent, wherein said solubilizing agent increases the solubility of said active principle by more than 50% when said solubilizing agent is placed in an aqueous solution at a concentration of 20% w/w at 37° C.;
wherein the at least one solubilizing agent is selected from the group consisting of hydrophilic polymers, polyvinyl pyrrolidone, polyvinyl alcohol, hydrophilic derivatives of cellulose, hydroxypropylcellulose, carboxymethylcellulose, maltodextrins, polyethylene glycol, surfactants, polyoxyethylene-polyoxypropylene copolymers, polyoxyethylenated hydrogenated castor oil, sodium dodecyl sulfate, esters of sucrose or sorbitan, phospholipids, polyethylene glycol stearate, disodium palmoate, polyoxyethylenated oils, polysorbates, sequestering agents, cyclodextrins, and mixtures thereof;
wherein the mass fraction [solubilizing agent]×100/[solubilizing agent+AP] is greater than or equal to 5%;
wherein said solubilizing agent confers properties upon the core such that in a dissolving test (TD) a non-coated core releases 80% of said active principle in less than two hours;
wherein the core is coated with a coating film which controls the modified release of the active principles;
wherein the coating film is at least 3% dry weight/dry weight of the microcapsule mass;
wherein the coating film comprises at least one film-forming polymer (P1) insoluble in gastrointestinal tract fluids, at least one water-soluble polymer (P2), and at least one plasticizer, (PL), wherein
the mass fraction by dry weight of P1 relative to the total mass of the coating is between 40 and 90%;
Wherein the mass fraction by dry weight P2/(P1+P2) is between 15 and 60%; and
Wherein the mass fraction by dry weight PL/(P1+PL) is between 1 and 30%.

2. The microcapsules of claim 1, wherein P1 is selected from the group consisting of water-insoluble derivatives of cellulose, ethylcellulose, cellulose acetate, acrylic derivatives, poly(vinyl acetates), and mixtures thereof.

3. The microcapsules of claim 1, wherein P2 is selected from the group consisting of water-soluble derivatives of cellulose, polyacrylamides, poly-N-vinylamides, poly (N-vinyl lactams), polyvinyl alcohols, polyoxyethylenes, polyvinylpyrrolidones, and mixtures thereof.

4. The microcapsules of claim 1, wherein PL is selected from the group consisting of glycerol, glycerol esters, acetylated glycerides, glyceryl monostearate, glyceryl triacetate, glyceryl tributyrate, phthalates, dibutyl phthalate, diethyl phthalate, dimethyl phthalate, dioctyl phthalate, citrates, acetyl tributyl citrate, acetyl triethyl citrate, tributyl citrate, triethyl citrate, sebacates, diethyl sebacate, dibutyl sebacate, adipates, azelates, benzoates, plant oils, fumarates, diethyl fumarate, malates, diethyl malate, oxalates, diethyl oxalate, succinates, dibutyl succinate, butyrates, cetyl alcohol esters, malonates, diethyl malonate, castor oil and mixtures thereof.

5. The microcapsules of claim 1, wherein the at least one active principle is selected from the group consisting of antiulcer agents, antidiabetic agents, anticoagulants, antithrombics, blood lipid-lowering agents, antiarrhythmics, vasodilators, antiangina agents, antihypertensives, vasoprotective agents, fertility promoters, inducers and inhibitors of uterine labor, contraceptives, antibiotics, antifungal agents, antiviral agents, anticancer agents, anti-inflammatories, analgesics, antiepileptics, antiparkinsonian agents, neuroleptics, hypnotics, anxiolytics, psychostimulants, antimigraine agents, antidepressives, antitussives, antihistamines, antiallergic agents, and mixtures thereof.

6. The microcapsules of claim 5, wherein the at least one active principle is selected from the group consisting of prazosine, acyclovir, nifedipine, naproxen, ibuprofen, ketoprofen, fenoprofen, indomethacine, diclofenac, sulpiride, terfenadine, carbamazepine, fluoxetine, alprazolam, famotidine, ganciclovir, spironolactone, acetylsalicyclic acid, quinidine, morphine, amoxicillin, paracetamol, metoclopramide, verapamil and mixtures thereof.

7. The microcapsules of claim 1, wherein the coating film further comprises at least one lubricating surfactant (TA).

8. The microcapsules of claim 7, wherein the TA is in a proportion of between 2 and 20% of the total mass of the dry coating.

9. The microcapsules of claim 7, wherein the TA is selected from the group consisting of anionic surfactants, alkali metal salts, alkaline-earth metal salts of fatty acids, stearic acid, oleic acid, nonionic surfactants, polyoxyethylenated oils, polyoxyethylenated hydrogenated castor oil, polyoxyethylene-polyoxypropylene copolymers, polyoxyethylenated sorbitan esters, polyoxyethylenated castor oil derivatives, stearates, calcium stearate, magnesium stearate, aluminum stearate, zinc stearate, stearyl fumarates, sodium stearyl fumarate, glyceryl behenate, and mixtures thereof.

10. A medicinal product comprising the microcapsules of claim 1.

11. The medicinal product of claim 10, wherein the product is in a form selected from the group consisting of tablet, gelatin capsule, powder, and aqueous suspension.

12. A medicinal product which comprises at least one active principle with low solubility, wherein the product is administered orally and released in vivo in a controlled, prolonged and, delayed manner,
    wherein the medicinal product comprises microcapsules with a mean diameter of less than 1000 microns;
    wherein each microcapsule has a core comprising at least one active principle and at least one solubilizing agent,
    wherein the core is coated with a coating film comprising at least one film-forming polymer (P1) insoluble in gastrointestinal tract fluids, at least one water-soluble polymer (P2), and at least one plasticizer (PL),
    wherein the coating film is at least 3% dry weight/dry weight of their total mass, and
    wherein the at least one solubilizing agent is one which when placed in an aqueous solution at a concentration of 20% w/w at 37° C. increases the solubility of the active principle by more than 50%,
    wherein the mass fraction by dry weight of P1 relative to the total mass of the coating is between 40 and 90%;
    Wherein the mass fraction by dry weight P2/(P1+P2) is between 15 and 60%; and
    Wherein the mass fraction by dry weight PL/(P1+PL) is between 1 and 30%.

13. The microcapsules of claim 7,
    wherein the mass fraction by dry weight of P1 relative to the total mass of the coating is between 50 and 80%;
    Wherein the mass fraction by dry weight P2/(P1+P2) is between 15 and 55%; and
    Wherein the mass fraction by dry weight PL/(P1+PL) is between 1 and 25%;
    wherein the mass fraction by dry weight of TA relative to the total mass of the coating is between 4 and 15%.

14. The microcapsules of claim 1, wherein said active principle is spironolactone and said solubilizing agent is polyoxyethylenated 40 hydrogenated castor oil.

* * * * *